(12) United States Patent
Strehl (10) Patent No.: US 9,226,700 B2
(45) Date of Patent: Jan. 5, 2016

(54) DETECTION ELEMENT FOR DETERMINING THE POSITION OF A LANCET ELEMENT IN A LANCING DEVICE

(75) Inventor: Michael Strehl, Pfreimd (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 185 days.

(21) Appl. No.: 13/514,034

(22) PCT Filed: Nov. 5, 2010

(86) PCT No.: PCT/EP2010/066911
§ 371 (c)(1),
(2), (4) Date: Jul. 3, 2012

(87) PCT Pub. No.: WO2011/069758
PCT Pub. Date: Jun. 16, 2011

(65) Prior Publication Data
US 2012/0265231 A1  Oct. 18, 2012

(30) Foreign Application Priority Data

Dec. 11, 2009 (DE) .......................... 10 2009 057 892
Mar. 6, 2010 (DE) .......................... 10 2010 010 507

(51) Int. Cl.
*A61B 5/15* (2006.01)
(52) U.S. Cl.
CPC .................................. *A61B 5/1411* (2013.01)
(58) Field of Classification Search
CPC ...... A61B 5/145; A61B 5/157; A61B 5/1411; A61B 5/1433; A61B 5/1444; A61B 5/15142; A61B 5/15186; A61B 5/150053; A61B 5/150167; A61B 5/151; A61B 5/15188; A61B 5/1519; A61B 5/15192
USPC .......................... 606/181, 182, 183, 184, 185
See application file for complete search history.

(56) References Cited

U.S. PATENT DOCUMENTS

| 4,442,836 | A | * | 4/1984 | Meinecke et al. | 606/182 |
| 4,628,929 | A | * | 12/1986 | Intengan et al. | 606/182 |
| 5,908,434 | A | * | 6/1999 | Schraga | 606/181 |
| 6,042,595 | A | * | 3/2000 | Morita | 606/181 |
| 6,852,119 | B1 | * | 2/2005 | Abulhaj et al. | 606/182 |
| 7,481,819 | B2 | * | 1/2009 | Koeppel et al. | 606/182 |

(Continued)

FOREIGN PATENT DOCUMENTS

| EP | 1614383 | 1/2006 |
| EP | 1913872 | 4/2008 |

(Continued)

*Primary Examiner* — Ryan Severson
*Assistant Examiner* — Christian Knauss
(74) *Attorney, Agent, or Firm* — Lowe Graham Jones PLLC (57) ABSTRACT

The present invention provides a detection element for lancets in lancing devices which will indicate that a lancet element is inserted completely again after the lancet has been changed. The invention includes a blood lancet apparatus which has a base body for the arrangement of a plurality of apparatus components, comprising a lancet reception device for coupling the blood lancet apparatus to a lancet element, at least one spring element for acting upon the lancet reception device with spring force and an actuating element for initiating a movement of the lancet reception device. The invention may further comprise a detection device for emitting at least for a time a signal with respect to a fixing position of the lancet element coupled at least in part to the lancet apparatus.

9 Claims, 10 Drawing Sheets

(56) References Cited

U.S. PATENT DOCUMENTS

| | | | |
|---|---|---|---|
| 7,775,991 B2* | 8/2010 | Feaster et al. | 600/584 |
| 8,118,825 B2* | 2/2012 | Schraga | A61B 5/1411 606/182 |
| 2003/0208162 A1* | 11/2003 | Crawford | 604/171 |
| 2004/0039407 A1* | 2/2004 | Schraga | 606/181 |
| 2004/0225311 A1* | 11/2004 | Levaughn et al. | 606/181 |
| 2006/0259059 A1* | 11/2006 | Marshall et al. | 606/181 |
| 2007/0049959 A1* | 3/2007 | Feaster et al. | 606/181 |
| 2007/0185515 A1* | 8/2007 | Stout | 606/181 |
| 2007/0255302 A1* | 11/2007 | Koeppel et al. | 606/182 |
| 2007/0293883 A1* | 12/2007 | Horie | 606/181 |
| 2008/0021493 A1* | 1/2008 | Levaughn et al. | 606/181 |
| 2008/0039886 A1* | 2/2008 | Shi | 606/182 |
| 2008/0077168 A1* | 3/2008 | Nicholls et al. | 606/182 |
| 2008/0140105 A1* | 6/2008 | Zhong et al. | 606/182 |
| 2009/0099431 A1 | 4/2009 | Dalebout et al. | |
| 2009/0099586 A1* | 4/2009 | Koeppel et al. | 606/182 |
| 2010/0030249 A1* | 2/2010 | Pusey et al. | 606/181 |
| 2010/0324582 A1* | 12/2010 | Nicholls et al. | 606/182 |

FOREIGN PATENT DOCUMENTS

| | | |
|---|---|---|
| WO | 2007104960 | 9/2007 |
| WO | 2007108967 | 9/2007 |

* cited by examiner

DETECTION ELEMENT FOR DETERMINING THE POSITION OF A LANCET ELEMENT IN A LANCING DEVICE

PRIORITY CLAIM

This invention claims priority from PCT Application Serial No. PCT/EP2010/066911 filed on Nov. 5, 2010 which claims priority to German Application Serial No. 102010010507.4 filed on Mar. 6, 2010 which claims priority to German Application Serial No. 102009057892.7 filed on Dec. 11, 2009, which are hereby incorporated by reference.

FIELD OF THE INVENTION

The invention relates to a detection element for lancets in lancing devices.

BACKGROUND OF THE INVENTION

Until now it has been customary for lancets or lancet elements—even if they are arranged inside a lancet holder inside a lancing device for piercing the skin for taking a blood sample—to have to be withdrawn by hand from the casing or the lancet holder of the lancing device when changing the lancet. In this case the problem arises that there is the risk of an inadvertent injury on the one hand and that it is necessary to handle lancets or lancet elements contaminated by blood from the puncture made previously on the other hand.

In addition, when changing the lancet or lancet element it has not been possible to ascertain whether the lancet has been inserted in a reliable manner, i.e. preferably up to 100 percent in the lancet holder, or is positioned at the intended location, so that a reliable operation of the lancing device, even with respect to the depth of piercing, may be guaranteed.

SUMMARY OF THE INVENTION

The present invention provides a detection element for lancets in lancing devices which will indicate that a lancet element is inserted completely again after the lancet has been changed.

A preferred embodiment of the present invention includes a blood lancet apparatus which has a base body for the arrangement of a plurality of apparatus components, comprising a lancet reception device for coupling the blood lancet apparatus to a lancet element, at least one spring element for acting upon the lancet reception device with spring force and an actuating element for initiating a movement of the lancet reception device. According to the invention a detection device for emitting at least for a time at least one signal with respect to a fixing position of the lancet element coupled at least in part to the lancet apparatus is provided in the region of the lancet reception device.

The fixing position is first of all understood to be any position of the lancet element inside or in the region of the lancet reception device, in which case it is preferable for the fixing position to represent the optimum position of the lancet element in, at and/or on the lancet reception device in order to perform a penetration movement. It is particularly preferred for the fixing position to be a position in which the lancet element is positioned in such a way with respect to the lancet reception device that a defined piercing procedure is capable of being carried out.

In accordance with the present invention the blood lancet apparatus is advantageous since it allows an operator to ascertain when the replaced lancet element or the lancet element newly coupled to the blood lancet apparatus is situated in the optimum position or the fixing position respectively.

In a further preferred embodiment of the present invention the detection device is arranged inside the base body and is movable with respect to the lancet reception device. This is advantageous since on the one hand the detection device is protected from damage and soiling by the arrangement of the detection device inside the base body. In addition, this arrangement assists the simplicity of operation, since a direct interaction of the user or the operator with the detection device is not necessary. On the other hand, this feature is advantageous since a movement of the detection device with respect to the lancet reception device allows in a simple manner the generation of signals, preferably of signals relating to the position of the lancet element with respect to the lancet reception device.

In a further preferred embodiment of the present invention the lancet reception device has at least one guide for guiding the detection device. In this case a guide is preferably understood as being a sliding bearing which can be designed to be dry or lubricated. It is particularly preferred for a guide or a sliding bearing respectively to be a contact area, in particular a bearing face, a recess, a groove, a projection, or the like and/or combinations thereof. The detection device is preferably guided in the displacement direction of the lancet reception device, in which case it is likewise possible for the detection device to be guided on a path at an inclination to it or on a curved path or combinations of such paths respectively. It is of course likewise possible for the guide to be formed on the base body, on further devices and/or by the interaction of a plurality of devices and/or the base body.

This embodiment is advantageous since a defined actuation of the detection device and thus a precise signal emission or positioning of the lancet element respectively are possible in this way.

In a further preferred embodiment of the present invention the detection device has a spring element for storing energy at least for a time, it being possible for the energy to be discharged substantially abruptly. A spring element is understood in this context as being any component which is suitable for storing energy and which can release this energy again at a defined time or in a defined situation respectively. The storage of the energy at least for a time is advantageous since it is possible for the spring element to supply the energy completely for a time or always to have a defined pre-stressing. In this case "capable of being discharged abruptly" is to be understood to mean that the energy which is stored in the spring element is discharged or is discharged in part within a period of time of less than 2 seconds, preferably <1 second and in a particularly preferred manner <0.5 seconds after the lifting of the overlying component, i.e. the release of the spring element. The introduction or the discharge of the energy can take place in a partly continuous or in a partly discontinuous manner in this case.

This embodiment is advantageous since even a small amount of energy allows the emission of a signal capable of being detected by an operator in the event of an abrupt discharge.

In a further preferred embodiment of the present invention the energy is capable of being supplied by means of an application of force upon the lancet element. To this end the lancet element is indirectly or preferably directly in contact with the detection device, and this causes an additional feedback message when the fixing position has been reached, since the insertion of the lancet element is then preferably prevented or braked or blocked by the detection device.

In a further preferred embodiment of the present invention a force absorption device, preferably a wedge, is provided in the interior of the base body, preferably on the lancet reception device, in order to absorb at least in part the force introduced into the spring element. In this case it is likewise possible for the force absorption device to be arranged inside the base body on the wall of the base body or a further device different from the lancet reception device or on the lancet reception device and any other further device. A force absorption device is preferably used as a resistance against which the spring element is capable of being moved in order to deflect the spring element. The force absorption device can be designed locally in the form of a wedge or can be made in a wedge shape and/or having curved portions.

This embodiment is advantageous since the generation or introduction of the energy respectively required for the emission of signals is possible when using the lancet element and thus by means of an operating step which is necessary in any case.

In a further preferred embodiment of the present invention, in order to secure a position of the detection device with respect to the lancet reception device and/or in order to emit the signal, which is preferably an acoustic and/or a haptic signal, the detection device has a snap element for co-operation with the force absorption device. As well as haptic and/or acoustic signals it is likewise possible for optical signals or an optical signal respectively to be capable of being emitted for example through the body of the wall or by means of a display unit instead of the signals named above or in combination with these signals. The snap element is preferably the spring element or the spring element is preferably designed in the form of a snap element, in which case embodiments are also possible in which additional spring elements or snap elements are provided.

This embodiment is advantageous since a snapping movement can be carried out inside the blood lancet apparatus by means of a snap element, as a result of which at least one acoustic and/or one haptic signal is emitted. In this case the acoustic signal is preferably a click which is representative of the snapping movement or the locking of the snap element and the haptic signal is preferably a vibration, which is produced for example by the snapping movement or the striking of the snap element against preferably further elements arranged in the blood lancet apparatus.

In a further preferred embodiment of the present invention a fixing and/or output device is provided for changing the coupling between the lancet reception device and the lancet element and for deflecting the spring element of the detection device. The fixing and/or output device is preferably used for manual actuation and, to this end, has a manual actuation device in a particularly preferred manner, in which case it is likewise possible for the fixing and/or output device or individual functions which are carried out by the fixing and/or output device to be carried out by further devices in a manual, automated or partially automated manner. A change of the coupling between the lancet reception device and the lancet element preferably signifies a change of a friction and/or positive locking which is present between the lancet reception device and the lancet element in the coupled state. It is possible for the change of the coupling and the deflection of the spring element to be carried out at the same time, offset in time or for a time at the same time by means of the fixing and/or output device.

This embodiment is advantageous since on account of the actuation or movement, in particular on account of the displacement of the fixing and/or output device, a number of functions are capable of being carried out in one operation, i.e. for example the single displacement of the fixing and/or output device in one direction.

In a further preferred embodiment of the present invention, in order to deflect the spring element, the fixing and/or output device has a preferably wedge-shaped first contact element which is capable of being brought into contact with a second contact element formed on the snap element in order to deflect the snap element. In this context "wedge-shaped" preferably describes a portion which is inclined with respect to the plane of the component and which can thus be made flat at least in part and/or curved at least in part. It is likewise possible for the second contact element to be made wedge-shaped. It is preferable for at least one of the contact elements to be made wedge-shaped, and the plane of the component is preferably formed from the longitudinal direction and the width-wise direction or depth-wise direction of the blood lancet apparatus. This embodiment is advantageous since the fixing and/or output device is capable of being brought into contact in a simple manner with the second contact element and thus with the snap element for deflecting the snap element.

In a further preferred embodiment of the present invention the detection device has a component body which extends perceptibly in one plane and on which the spring element is designed in the form of a tongue-like portion opposite a tongue-like reinforcement portion, in which case the second contact element, which forms at least one curved portion, extends substantially at a right angle to the plane of the component in the region of one end of the spring element. A contact edge or contact face, by which the body of the component is capable of being brought into contact with the lancet element, is preferably provided on the body of the component.

This embodiment is advantageous since the detection device forms an intermediate element which in an advantageous manner can preferably co-operate indirectly or preferably directly at least for a time with a plurality of components, such as for example the lancet reception device, the lancet element and/or the fixing and/or output device.

A detection element of this type is to be understood as being a part which is designed in the form of a separate component and is preferably directly or indirectly in contact for a time with the rear side of the lancet or even the lancet holding apparatus. This separate component can generate a noise by means of a snap closure or snap element when the lancet element is inserted, in particular in the event of a displacement of the lancet element directed towards the rear or towards the inside, it being preferable for the detection element to be displaceable by the application of force to the lancet element at least for a time. In this way, the component generates a noise by a snapping procedure as soon as the newly inserted lancet element has been completely inserted into the blood lancet apparatus and thus into the lancet reception device or the lancet holder respectively. The user can thus be certain that at this moment the lancet is completely connected to the lancet holding apparatus.

In addition, it becomes possible, as a result, that lancet elements of the most widely varying type, which for example have no stop ring in the front region on their external peripheral side, can be used, without there being a risk that the lancet is not completely inserted into the lancet reception device.

It is likewise possible for the spring element not to be formed on the detection device but for a force absorption device to be formed on the detection device and for the spring element to be arranged on the base body of the blood lancet apparatus, the lancet reception device or a further component inside the blood lancet apparatus. It is likewise possible for a snap element to be formed on the lancet element.

BRIEF DESCRIPTION OF THE DRAWINGS

Further advantages, aims and properties of the present invention are explained with reference to the following description of accompanying drawings, in which blood lancet apparatus and individual components of blood lancet apparatus are illustrated by way of example. Components of the blood lancet apparatus, which correspond at least substantially with respect to their function in the figures, may not be numbered and explained in all the figures for the sake of clarity.

DETAILED DESCRIPTION OF THE PREFERRED EMBODIMENT

Figure 1:
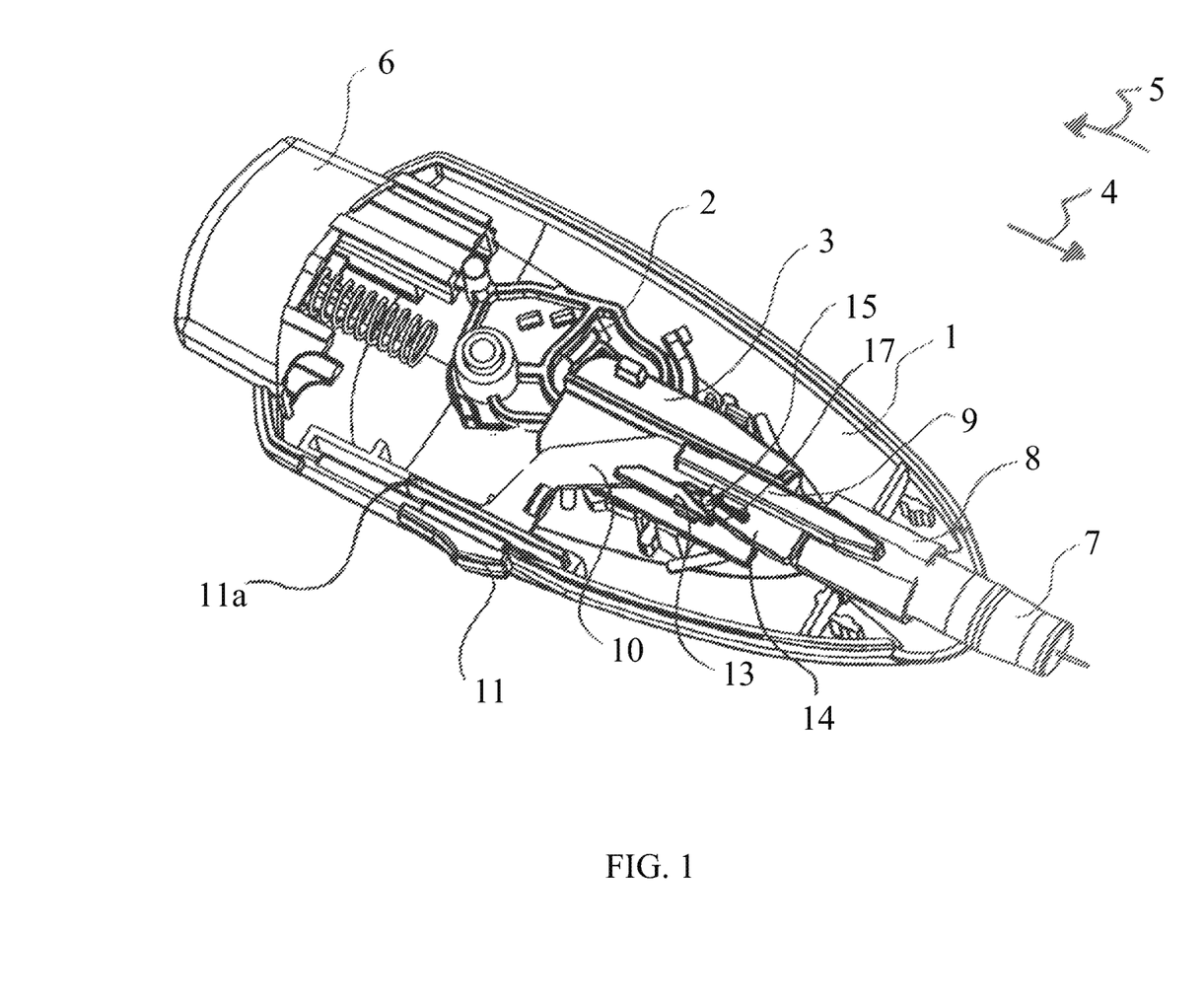
FIG. 1 is a cut-way illustration of a lancing device according to one embodiment of the present invention by way of example.

A cut-way illustration of a lancing device according to one embodiment of the invention by way of example is shown in FIG. 1. The upper portion of the casing is not shown in this illustration.

The lower base body 1 or the lower casing portion respectively has inter alia a control cam element 2 which is preferably passed by the lancet reception device 3 during the piercing procedure by a pin (not shown in detail here) in order to displace the lancet reception device 3 in the forward direction 4 or the rearward direction 5. This procedure can preferably be initiated by a push button (not shown here). The push button 6 attached at the rear is used for exerting a force for pre-stressing a spring which acts directly or indirectly upon the control cam element 2.

In addition, FIG. 1 shows a lancet element 7 which is arranged in a front portion 8 of the lancet reception device 3. In this illustration a rod-shaped element 9 with a wedge-shaped tip for widening the front portion 8—which preferably has at least one gap—of the lancet reception device 3 is inserted at least in part into the front portion 8. The widening or deformation of the front portion 8 has the effect that a friction locking and/or a positive locking which exists between the front element 8 and the lancet element 7 is unchanged or is formed or discontinued.

The rod-shaped element 9 is preferably an integral component of the fixing and/or output device 10, it likewise being possible for the rod-shaped element 9 to be attached to the fixing and/or output device 10 or to a further device.

The fixing and/or output device 10 preferably has a manual actuation element 11 and a guide device 11a. The manual actuation element 11 is used for displacing the fixing and/or output device 10 as a whole, and the guide device 11a is used in a particularly preferred manner to ensure a defined displacement movement, in which case the guide device 11a co-operates with a further device and/or the base body in the form of a sliding bearing or slide.

Furthermore, the fixing and/or output device 10 has formed on it a first contact element 13 which has a preferably wedge-shaped tip for bringing into contact with a detection device 14, in particular with a second contact element 15 which is formed on the detection device 14.

In this illustration the second contact element 15 is designed in the form of a pin element and it extends preferably at a right angle to the displacement movement 4 and thus in the vertical direction of the base body 1. It is preferable for at least one tongue-shaped fastening plate or rod part of the detection device 14, which in a particularly preferred manner is designed in the form of a snap device, to be attached as an element with positive locking—which can co-operate with the force absorption device 16 (not shown in this illustration) to generate a spring force and/or fixing, in particular a positive locking, or to emit or produce a signal—to the spring element 17 below the second contact element 15 in the vertical direction.

Figure 2:
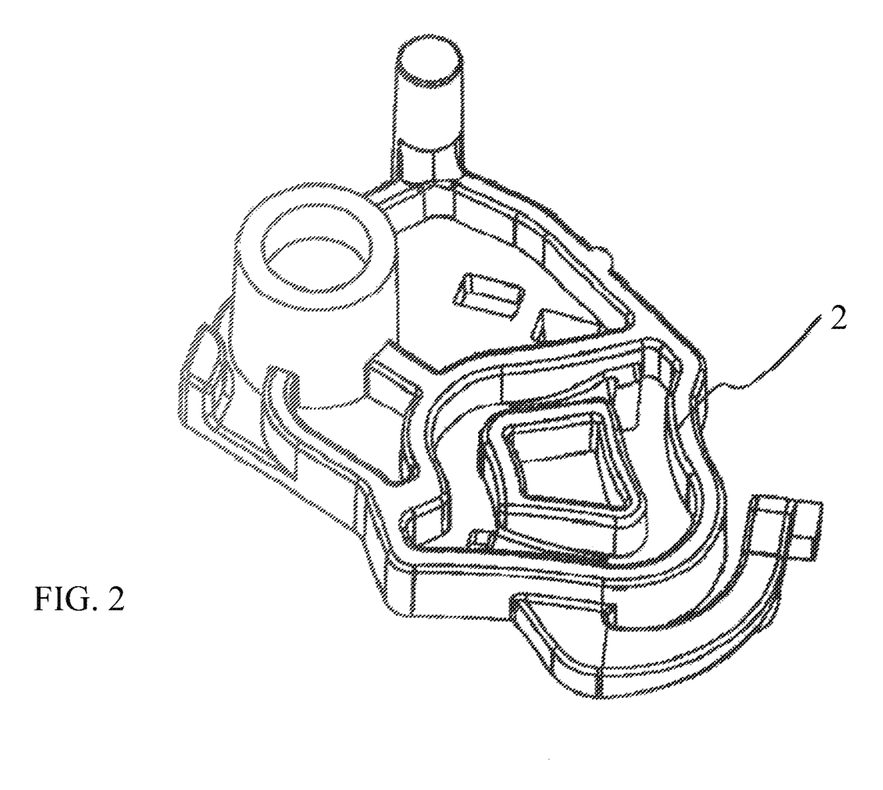
FIG. 2 shows a cam element which is suitable for use in a blood lancet apparatus according to the present invention.

FIG. 2 shows by way of example a curved path, which is designed in such a way that it causes a displacement of the lancet reception device 3 and thus of the lancet element 7 in the extension direction 4 and the insertion direction 5 in a manner dependent upon a force exerted.

Figure 3:
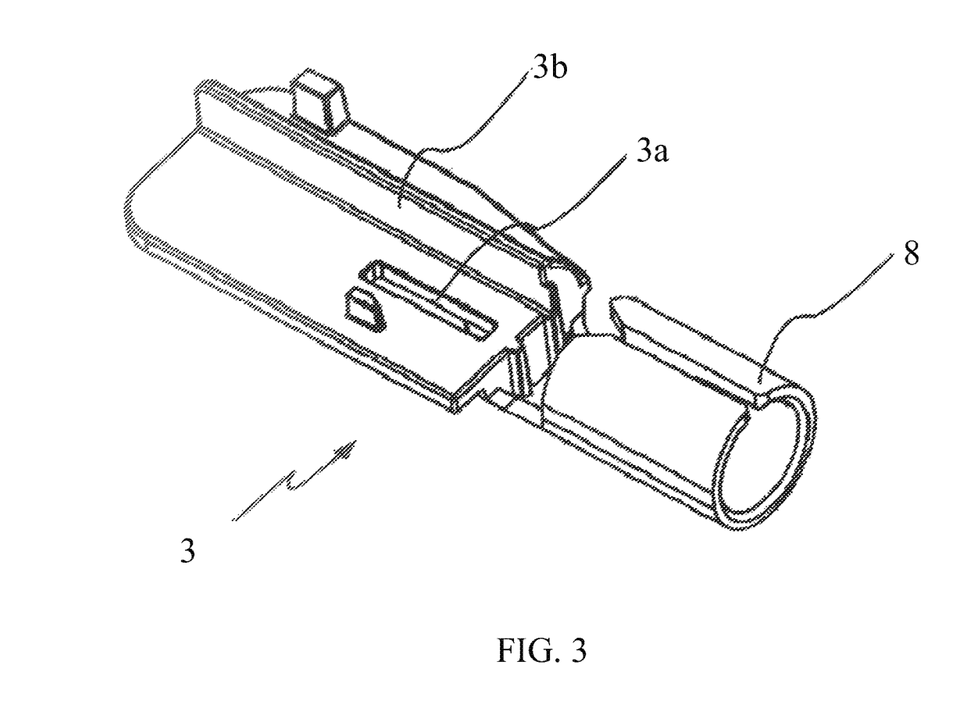
FIG. 3 shows a lancet reception device which is suitable for use in a blood lancet apparatus according to the present invention.

A lancet reception device 3 is shown in FIG. 3 by way of example. In this case the lancet reception device has at least one front portion 8 for receiving the lancet element 7. In addition, the lancet reception device 3 comprises a first guide 3a, which is preferably suitable for guiding the detection device 14, and a second guide 3b, which is preferably suitable for guiding or for bringing into contact with the rod-shaped element 9.

Figure 4:
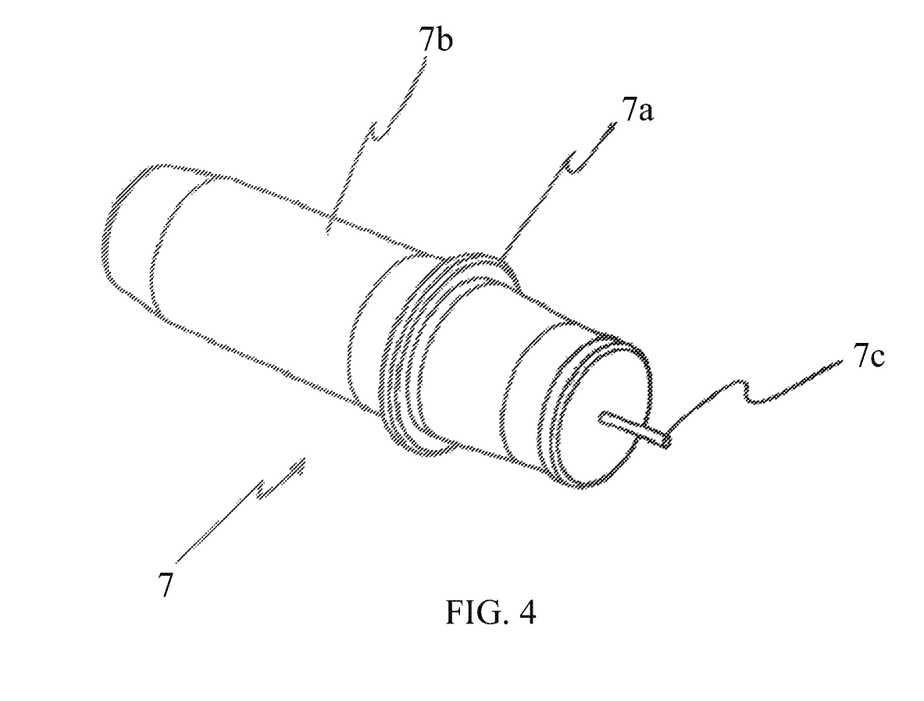
FIG. 4 shows a lancet element which can be used for example in the present invention.

FIG. 4 shows a lancet element 7 by way of example which has a ring 7a on the lancet body 7b. The lancet 7c projects out of the lancet body 7b in the longitudinal direction of the latter. It is possible in this case for particularly lancet elements 7 to be capable of being inserted into the blood lancet apparatus according to the invention with and without the ring 7a.

Figure 5:
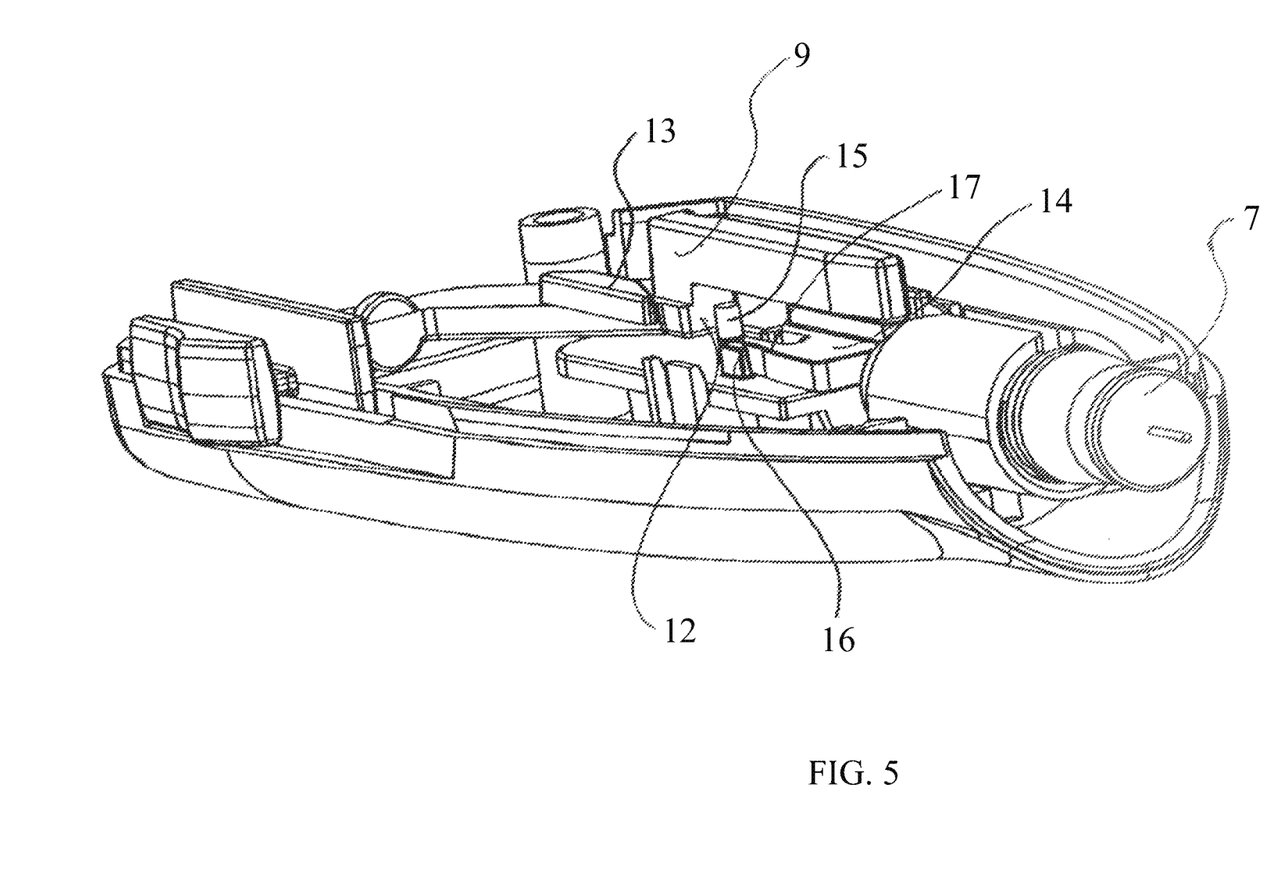
FIG. 5 is a perspective partial illustration by way of example of a blood lancet apparatus according to the present invention in a first setting.

A first contact element 13 formed in a wedge shape may be seen in FIG. 5, this contact element 13 having the task that the component causing the noise relevant to the invention, i.e. the detection device 14, may release in particular the spring element 17 with a projection—which is formed on it and which can be designed in the manner of a pin—from a catch movement or position.

In a preferred embodiment, the second contact element 15 or the pin 15 respectively is released during a shifting of the fixing and/or output device 10 forwards out of an anchoring with respect to the force absorption device 16, which is designed for example in the form of a projection 16, and this leads to the spring element 17—which is designed for example in the form of a tongue element 17 of the detection device 14—being deformed or deflected. This deflection of the spring element 17 leads to the second contact element 15 being released from a locking with respect to the projection 16 or the force absorption device 16 respectively and, as a result, the detection device 14 preferably being displaced forwards or in the direction 4 together with the fixing and/or output device 10.

Figure 6:
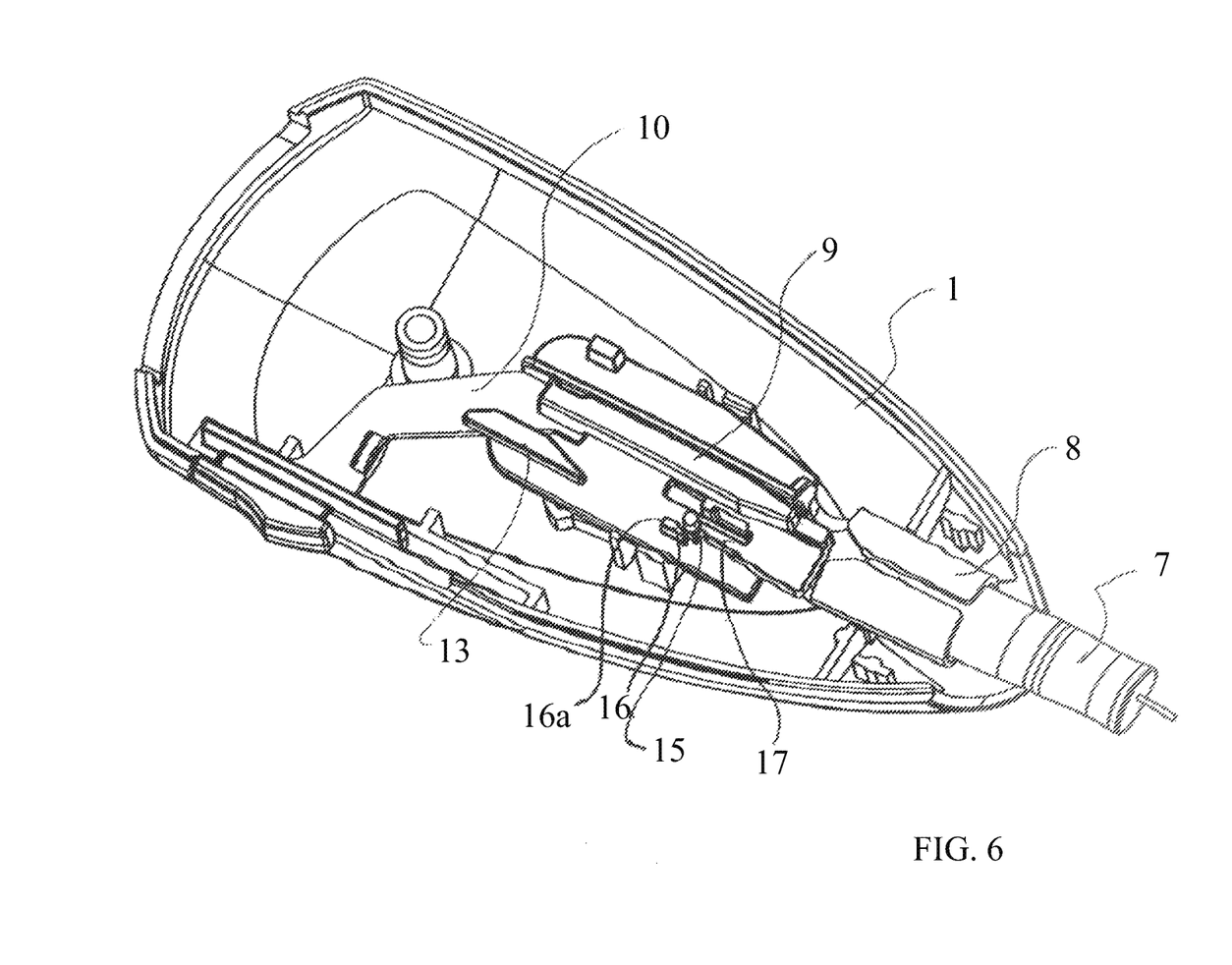
FIG. 6 shows a first arrangement by way of example in the time sequence of inserting a new lancet.
Figure 7:
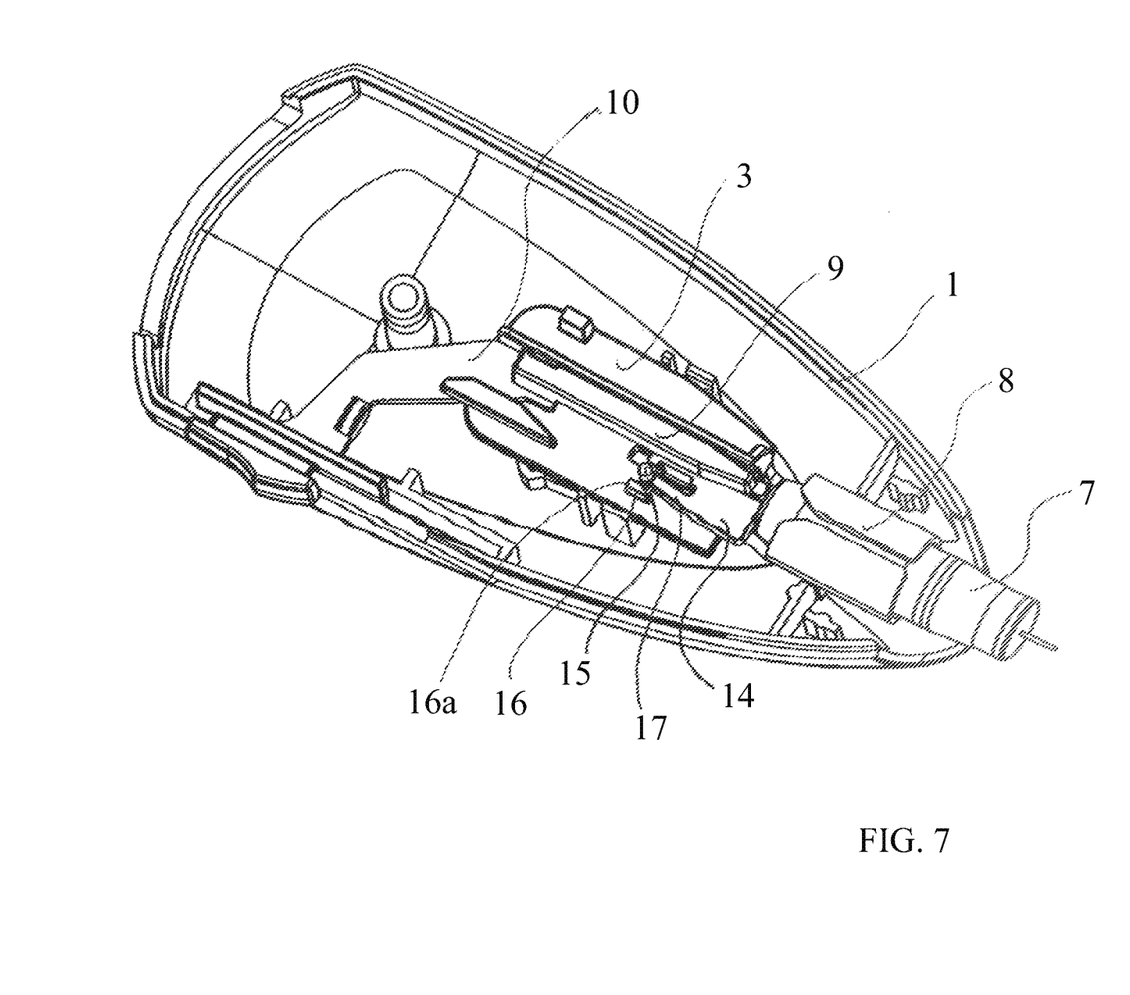
FIG. 7 shows a second arrangement by way of example in the time sequence of inserting a new lancet.
Figure 8:
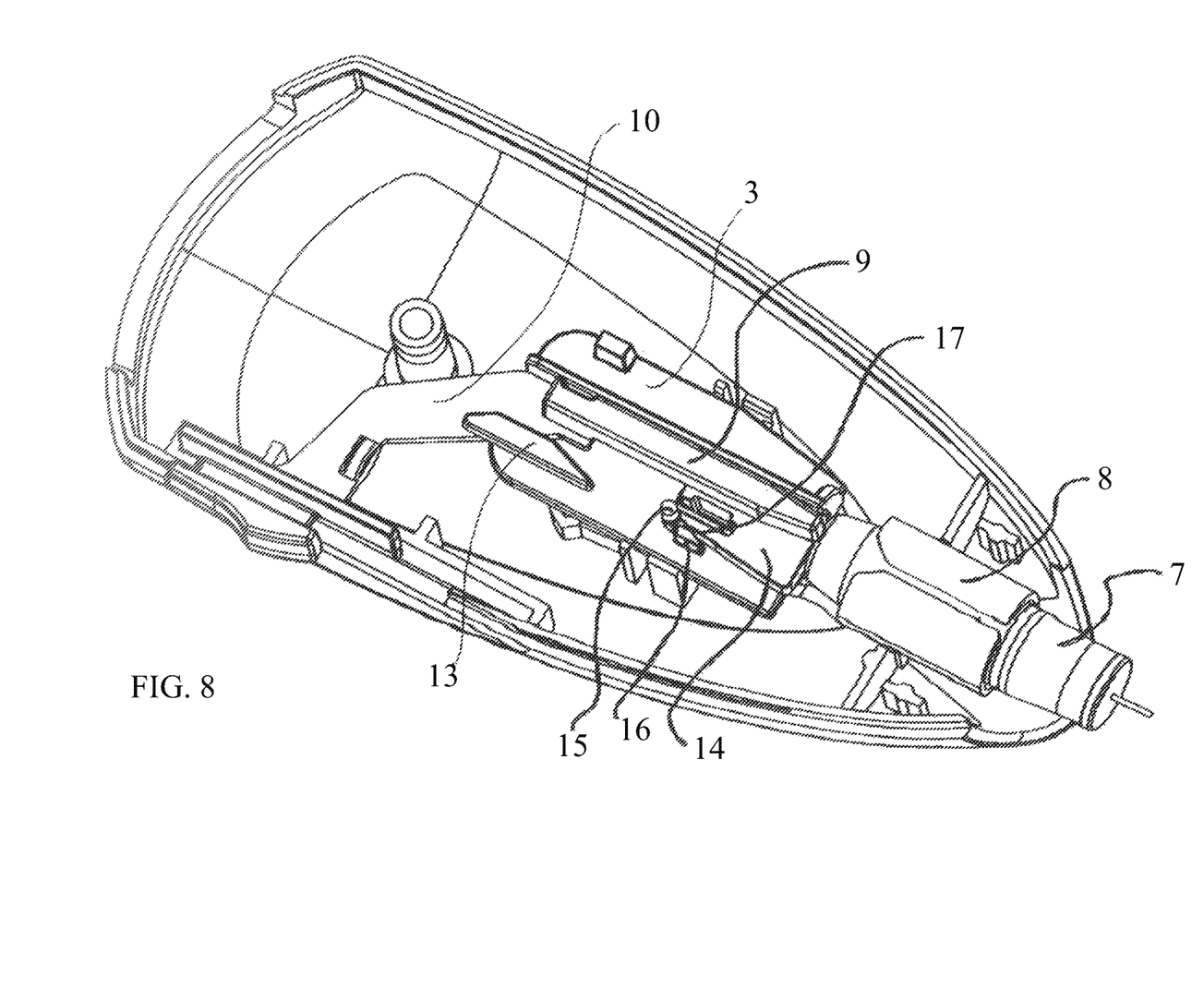
FIG. 8 shows a third arrangement by way of example in the time sequence of inserting a new lancet.

In FIGS. 6, 7 and 8 the time sequence of the insertion of a new lancet element 7 into the lancet reception device 3 and thus the blood lancet apparatus or lancing device is illustrated by way of example.

As shown in FIG. 6, the lancet element 7 is inserted into the cylindrical front portion 8. In this position the rod-shaped element 9 is preferably displaced to the rear or in the direction 5. In the same way, the fixing and/or output device 10 as a whole is preferably arranged in the rear position.

The second contact element 15 which is attached to the spring element 17 is not yet in engagement again, i.e. it is not yet situated on a rear side 16a of the force absorption device 16. It is in fact situated in front of the force absorption device 16 as viewed in the forward direction 4.

In FIG. 7 the second contact element 15 is already displaced a little further in the direction 5. At the same time the detection device 14 with the tongue attached to it or the spring element 17 formed on it respectively is displaced towards the inside or in the direction 5. This is carried out for example by the insertion of the lancet element 7 into a position directed further inwards inside the lancing device.

In FIG. 8 the lancet element 7 is now inserted completely into the lancet reception device 3. In this case the detection device 14 is displaced completely to the rear. In this way, the second contact element 15 or the portion situated thereunder and preferably forming an undercutting respectively is brought into engagement with respect to the force absorption device 16, by being positioned on the rear side 16a of the force absorption device 16. This positioning is carried out by a releasing procedure of the spring element 17, which is attached to the detection device 14. This releasing procedure has the effect that the spring element 17 is moved in the direction of the force absorption device 16.

Figure 9:
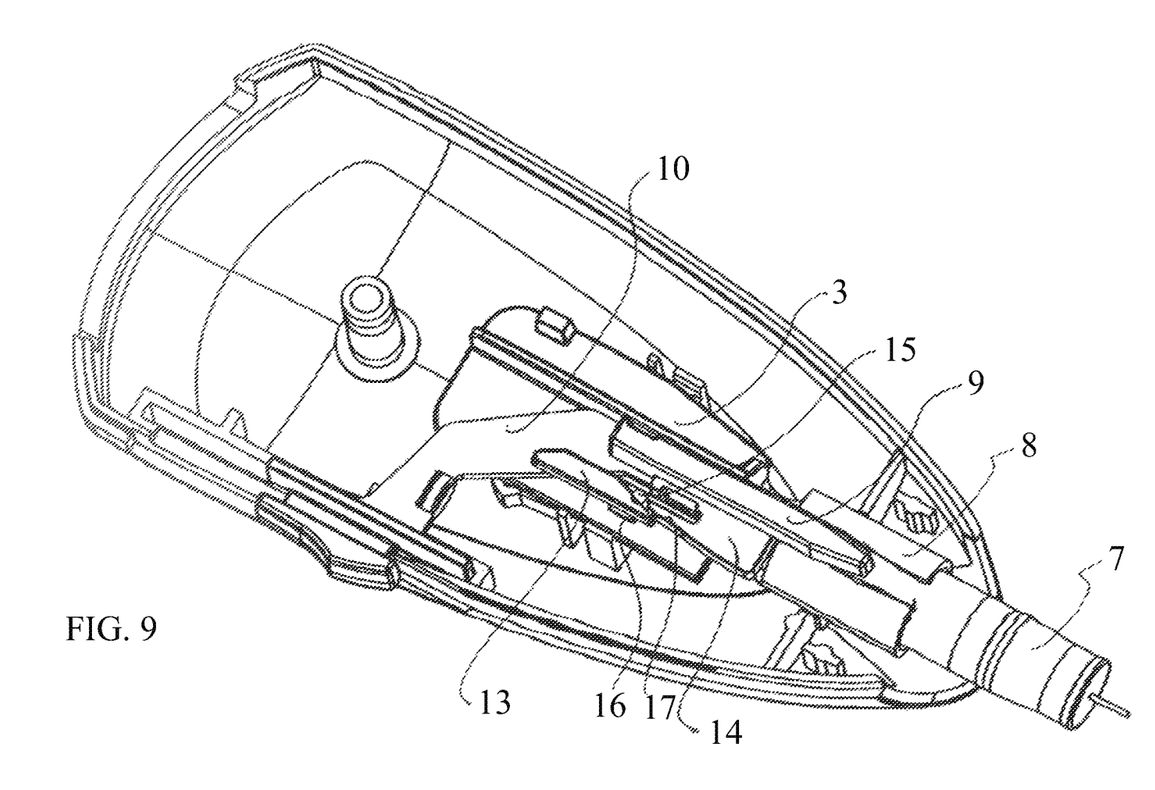
FIG. 9 is an illustration by way of example of an extension arrangement.

FIG. 1 and FIG. 9 show a position of the lancet, the lancet device 3 and the displacement element 10 in which the spreading element 9 has already spread the front cylindrical part 8 of the lancet holding device and in this way it is possible for the lancet or the lancet element 7 respectively to be removed.

The spring element 17 has a recess immediately in front of the second contact element 15, or the pin or the second contact element 15 respectively is arranged at an angle or projecting with respect to the lateral face 19 opposite the rest of the spring element 17. This is evident in FIG. 10, in which the detection device 14 with the spring element 17, the component body 18 forming the detection device 14 and the second contact element 15 is illustrated separately.

Figure 10:
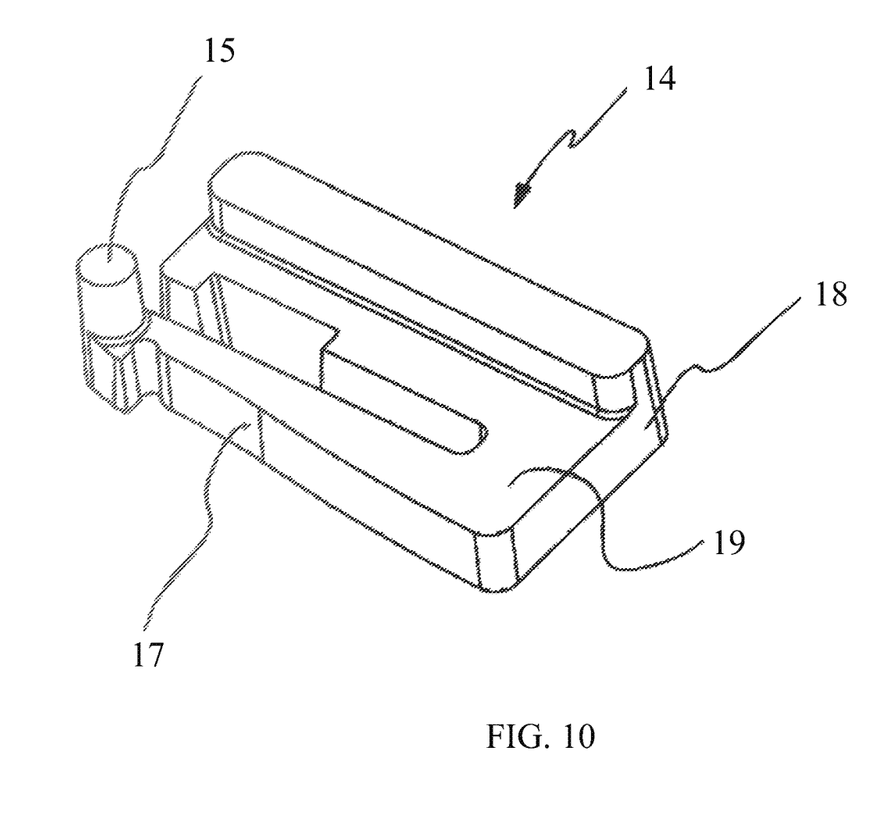
FIG. 10 is a perspective illustration by way of example of a detection device according to the invention.

On account of such an arrangement of the detection device 14, with each insertion of a new lancet element when the lancets are to be changed a locking of the pin or the second contact element 15 respectively with respect to the projection or the force absorption device 16 respectively can advantageously be achieved in a reliable manner only when the lancet element 7 has been inserted completely into the lancet reception device 3. This is advantageously indicated by a sound or a noise on the basis of the snapping procedure. The user will thus know that the lancet element 7 has been inserted completely into the lancing device or the blood lancet apparatus respectively.

The applicants reserve the right to claim all the features disclosed in the application documents as being essential to the invention, insofar as they are novel either individually or in combination as compared with the prior art.

The embodiments of the invention in which an exclusive property or privilege is claimed are defined as follows:

1. A blood lancet apparatus with a base body for the arrangement of a plurality of apparatus components, comprising:
   a lancet reception device for coupling the blood lancet apparatus to a lancet element;
   at least one lancet spring for acting upon the lancet reception device with spring force;
   an actuator for initiating a movement of the lancet reception device along a displacement direction that is substantially aligned with a longitudinal direction of the base body; and
   a detection device associated with the lancet reception device for emitting at least for a time at least one signal with respect to a fixing position of the lancet element coupled at least for a time and at least in part to the blood lancet apparatus, wherein the detection device is arranged inside the base body and arranged movable along the displacement direction with respect to the lancet reception device and comprises:
     a detection spring configured to store energy at least for a time, wherein the energy is capable of being discharged substantially abruptly; and
     an output device configured to change the coupling between the lancet reception device and the lancet element and to deflect the detection spring, wherein the output device comprises a rod-shaped element that allows and inhibits at least one of a friction locking or a positive locking between the lancet reception device and the lancet element,
   wherein the lancet reception device has at least one guidance for guiding the detection device in the displacement direction of the lancet reception device.

2. The apparatus according to claim 1, wherein the energy is capable of being supplied by means of an application of force upon the lancet element.

3. The apparatus according to claim 1, further comprising a force absorption device configured to absorb at least for a time and at least in part a force introduced into the detection spring.

4. The apparatus according to claim 3, wherein the force absorption device is wedge-shaped and associated with the lancet reception device.

5. The apparatus according to claim 1, wherein the detection device has a snap element for co-operation with a force absorption device in order to accomplish at least one of securing a position of the detection device with respect to the lancet reception device or emitting the signal, wherein the signal is at least one of an acoustic signal or a haptic signal.

6. The apparatus according to claim 5, wherein the emitted signal is one of an acoustic or a haptic signal.

7. The apparatus according to claim 5, wherein the output device comprises a wedge-shaped first contact element ent configured to contact a second contact element formed on the snap element in order to deflect the snap element.

8. The apparatus according to claim 7, wherein:
   the detection device further comprises a component body that extends perceptibly in one plane; and
   the detection spring is configured in the form of a tongue-like portion opposite a tongue-like reinforcement portion, wherein the second contact element forms at least one curved portion that extends at a right angle in a region of one end of the detection spring.

9. A blood lancet apparatus with a base body for the arrangement of a plurality of apparatus components, comprising:
   a lancet reception device for coupling the blood lancet apparatus to a lancet element;

at least one lancet spring for acting upon the lancet reception device with spring force;

an actuator for initiating a movement of the lancet reception device along a displacement direction that is substantially aligned with a longitudinal direction of the base body; and a detection device associated with the lancet reception device for emitting at least for a time at least one signal with respect to a fixing position of the lancet element coupled at least for a time and at least in part to the blood lancet apparatus, wherein the detection device is arranged inside the base body and arranged movable along the displacement direction and with respect to the lancet reception device and comprises:

a detection spring configured to store energy at least for a time, wherein the energy is capable of being discharged substantially abruptly;

an output device configured to change the coupling between the lancet reception device and the lancet element and to deflect the detection spring, wherein the output device comprises a wedge-shaped first contact element configured to contact a second contact element formed on a snap element in order to deflect the snap element and a second contact element;

wherein the lancet reception device has at least one guidance for guiding the detection device in the displacement direction of the lancet reception device, wherein the detection device further comprises the snap element for co-operation with a force absorption device in order to accomplish at least one of securing a position of the detection device with respect to the lancet reception device or emitting the at least one signal, wherein the at least one signal is at least one of an acoustic signal or a haptic signal, and a component body that extends perceptibly in one plane; and the detection spring is configured in the form of a tongue-like portion opposite a tongue-like reinforcement portion, wherein the second contact element forms at least one curved portion that extends at a right angle in a region of one end of the detection spring.

* * * * *